United States Patent [19]

Narisada et al.

[11] 4,211,779
[45] Jul. 8, 1980

[54] 7α-METHOXY SUBSTITUTED CEPHALOSPORINS

[75] Inventors: Masayuki Narisada, Ibaraki; Teruji Tsuji, Takatsuki; Hiromu Matsumura, Ashiya; Wataru Nagata, Nishinomiya, all of Japan

[73] Assignee: Shionogi & Co., Ltd., Osaka, Japan

[21] Appl. No.: 821,314

[22] Filed: Aug. 2, 1977

[30] Foreign Application Priority Data

Aug. 17, 1976 [JP] Japan .................................. 51-98376

[51] Int. Cl.$^2$ .................. A61K 31/545; C07D 501/36
[52] U.S. Cl. ........................................ 424/246; 544/21
[58] Field of Search ........................... 544/21; 424/246

[56] References Cited

U.S. PATENT DOCUMENTS

| 3,926,974 | 12/1975 | Nudelman et al. | 544/28 |
| 4,058,661 | 11/1977 | Cama et al. | 544/21 |
| 4,087,424 | 5/1978 | Saikawa et al. | 544/28 |
| 4,129,730 | 12/1978 | Saikawa et al. | 544/21 |

FOREIGN PATENT DOCUMENTS 2702552 7/1977 Fed. Rep. of Germany .
51-6117 1/1976 Japan .

Primary Examiner—Glennon H. Hollrah
Assistant Examiner—David E. Wheeler
Attorney, Agent, or Firm—Wenderoth, Lind & Ponack

[57] ABSTRACT

Antibacterial 7α-methoxy-3-cephem derivatives of the formula:

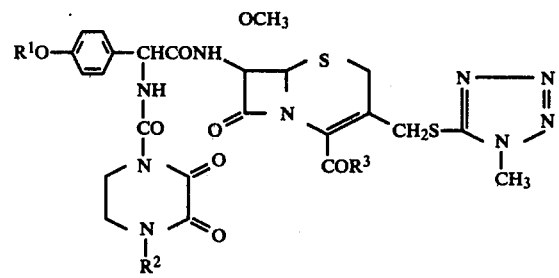

[wherein
$R^1$ is hydrogen, or organic or inorganic acyl;
$R^2$ is alkyl; and
$COR^3$ is carboxy or protected carboxy], methods of production, and pharmaceutical preparations thereof.

31 Claims, No Drawings

7α-METHOXY SUBSTITUTED CEPHALOSPORINS

This invention relates to antibacterial cephalosporins shown by the following formula, methods for their production, and pharmaceutical preparation containing said cephalosporins:

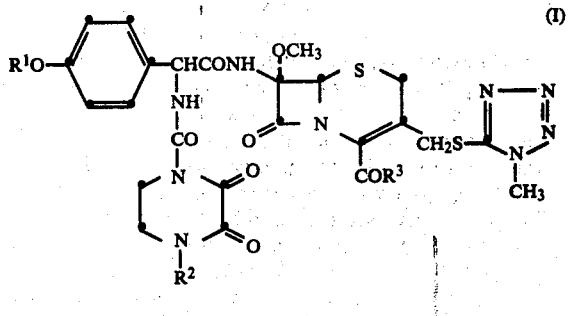

[wherein
$R^1$ is hydrogen, or organic or inorganic acyl;
$R^2$ is alkyl; and
$COR^3$ is carboxy or protected carboxy]

Representative of organic or inorganic acyl groups represented by $R^1$ are alkanoyl, aralkanoyl, aroyl, alkoxycarbonyl, aralkoxycarbonyl, carbamoyl, thiocarbamoyl, N-monosubstituted carbamoyl, N,N-disubstituted carbamoyl which may be substituted, and the like. Preferable acyl groups are $C_1$ to $C_3$ alkanoyl, carbamoyl, and $C_2$ to $C_4$ alkoxycarbonyl.

Alkyl group represented by $R^2$ means straight, branching, or cyclic alkyl. Preferable alkyl groups are $C_1$ to $C_4$ alkyl groups, particularly methyl and ethyl.

Protected carboxy represented by $COR^3$ means organic or inorganic salts (e.g. organic acid salts such as triethylamine salts, dicyclohexylamine salts and dimethylaniline salts, inorganic acid salts as alkali metal salts, alkaline earth metal salts, aliphatic or aromatic esters (e.g. alkyl esters which may be substituted, such as methyl, ethyl, t-butyl, 2,2,2-trichloroethyl, iodoethyl, cyanoethyl, mesylethyl, methoxymethyl, phenacyl and alkanoyloxymethyl esters; aralkyl esters which may be substituted, such as benzyl, p-methoxybenzyl, p-nitrobenzyl, diphenylmethyl, trityl and phthalidyl; aryl esters which may be substituted, such as phenyl, indan-5-yl, and benzothiazol-thio; metallic esters such as trimethylsilyl, dimethylsilyl and trimethylstannyl ester), amido, hydrazides, and other carboxy derivative-forming groups conventionally used in the chemistry of penicillins and cephalosporins.

Among the above salts or esters, those which may form pharmaceutically acceptable and absorbable compounds (e.g. alkali metal salts, alkaline earth metal salts, acyloxyalkyl esters, phthalidyl esters) are important in employing as drugs.

The other ones forming other salts, esters, amides, hydrazides, etc. are useful and convenient groups in intermediates for production. They have no important meaning in their specific structures, and highly changable.

Representatives of Compound (I) include these having following figures:

| $R^1$ | $R^2$ | $COR^3$ |
|---|---|---|
| hydrogen | methyl | carboxy |

-continued

| $R^1$ | $R^2$ | $COR^3$ |
|---|---|---|
| " | ethyl | " |
| " | propyl | " |
| " | isopropyl | " |
| " | butyl | " |
| " | sec-butyl | " |
| " | isobutyl | " |
| " | t-butyl | " |
| carbamoyl | methyl | " |
| " | ethyl | " |
| " | propyl | " |
| " | butyl | " |
| " | isobutyl | " |
| acetyl | methyl | " |
| " | ethyl | " |
| " | propyl | " |
| " | isobutyl | " |
| propionyl | methyl | " |
| " | ethyl | " |
| " | propyl | " |
| butyryl | methyl | " |
| " | ethyl | " |
| benzoyl | methyl | " |
| " | ethyl | " |
| thiocarbamoyl | " | " |
| methylthiocarbamoyl | " | " |
| dimethylcarbamoyl | " | " |
| trichloroacetylcarbamoyl | " | " |
| acetylcarbamoyl | " | " |
| methoxycarbonyl | methyl | " |
| " | ethyl | " |
| " | propyl | " |
| ethoxycarbonyl | methyl | " |
| " | ethyl | " |
| " | isopropyl | " |
| propoxycarbonyl | methyl | " |
| " | ethyl | " |
| " | butyl | " |
| isopropoxycarbonyl | methyl | " |
| " | ethyl | " |
| " | t-butyl | " |

The above compounds may be used in the form of a pharmaceutically acceptable salt.

Other representative specific compounds are those cited above but having protected carboxy ($COR^3$) for the convenience of synthesis, e.g. t-butyl, trichloroethyl, iodoethyl, benzyl, nitrobenzyl, methoxybenzyl, diphenylmethyl, trimethylsilyl, dimethylmethoxysilyl, or trimethylstannic ester; or triethylammonium, N-methylmorpholinium or dicyclohexylammonium salt.

Further groups of representative Compound (I) include the specific compounds cited above but having protected carboxy ($COR^3$) for the convenience of pharmaceutical usage, for example, a pharmaceutically acceptable salt, e.g. lithium, sodium, potassium, magnesium, calcium, or aluminum salt or a pharmaceutically acceptable ester, e.g. acetoxymethyl, pivaloyloxymethyl, methoxycarbonyloxymethyl, ethoxycarbonyloxyethyl, butoxycarbonyloxymethyl, phenacyl, phenyl, indanyl, or phthalidyl ester.

II. Prior Art

Compounds represented by the formula (I) having no 7α-methoxy are described in Japanese Patent Application Open to Public Inspection No. 51-70788.

III. Effects

Compounds (I) are strong antibacterials against gram positive and negative bacteria, and more potent than the said prior art compounds against microorganisms resistant to cephalosporins, e.g. strains of Proteus, Enterobacter, Serratia, Pseudomonas, and especially of *Escherichia coli* and *Klebsiella pneumoniae.*

IV. Preparation

Compounds (I) may be prepared by the following processes:

(1) Acylating 7β-amino-7α-methoxy-3-(1-methyl-1H-tetrazol-5-yl)-thiomethyl-3-cephem-4-carboxylic acid or derivatives thereof at the carboxy group, which may be activated in forms of isocyano, isocyanato, 1-haloalkylideneamino, 1-alkoxyalkylideneamino, silylamino, enamino, and the like, with reactive derivatives of α-p-hydroxyphenyl-N-(4-alkyl-2,3-dioxopiperazin-1-yl)carbonylglycine (e.g. free acid, acid halogenide, acid anhydride, active ester, active amide, or ketene), of which phenol group may be acylated, if required in the presence of active accelerator (e.g. a base, molecular sieve, carbodiimide, epoxide, EEDQ, or enzyme);

(2) Heating 7β-[α-p-hydroxyphenyl-N-(4-alkyl-2,3-dioxopiperazin-1-yl)carbonylglycyl]amino-7α-methoxycephalosporanic acid or salts thereof together with 1-methyl-5-mercapto-1H-tetrazole or salts thereof at 50° to 100° C. under neutral condition (particularly at pH 6.5 to 6.0);

(3) Introducing a methoxy group into the derivatives of Compounds (I) having a hydrogen at the 7α-position on treatment with e.g. lithium methoxide and t-butyl hypohalite in methanol;

(4) Treating 1-oxide derivatives of Compounds (I) with triarylphosphine, stannous chloride, or the like;

(5) Removing a carboxy protecting group from carboxy-protected Compounds (I) by hydrolysis, reduction, solvolysis, photochemical reaction, or other appropriate manners to the specific protecting groups;

(6) Reaction of 7β-(α-p-hydroxyphenylglycinamido)-7α-methoxy-3-(1-methyl-1H-tetrazol-5-yl)thiomethyl-3-cephem-4-carboxylic acid or derivatives thereof at the phenolic hydroxy and carboxy, with reactive derivatives of 4-alkyl-2,3-dioxopiperazin-1-yl-carboxylic acid;

(7) Salt formation of Compounds (I) having free carboxy group on treatment with bases or basic salts involving the desired cation part;

(8) Deprotecting the protected phenol group in Compounds (I) wherein $R^1$ is a phenolic hydroxy-protecting group to yield Compounds (I) wherein $R^1$ is hydrogen;

(9) Acylating Compounds (I) wherein $R^1$ is hydrogen to yield Compounds (I) wherein $R^1$ is acyl.

(10) Other processes conventionally used in the field of penicillin and cephalosporin chemistry.

V. Starting materials

All of the starting materials employed in the processes described above IV may be prepared from known materials such as 7-aminocephalosporanic acid in known manners.

Representatives of said known manners are:

(1) acylation to introduce p-hydroxyphenylglycyl, (2) introduction of 1-methyl-1H-tetrazol-5-thio group, (3) introduction of 7α-methoxy, (4) preparation of 1-oxide and reduction, (5) liberation of carboxy group, (6) salt formation, (7) deprotection of phenolic hydroxy-protecting group and acylation, (8) introduction of 4-alkyl-2,3-dioxopiperazin-1-yl-carbonyl, and (9) other manners, applicable in proper combination.

VI. Products

Unreacted starting materials, reagents, by-products, solvents and the like are removed in conventional manners such as extraction, washing, concentration, and drying, and the products prepared in each reaction may be purified in conventional manners such as recrystallization, reprecipitation, and chromatography.

Compounds (I) are novel antibacterial agents processing potent antibacterial activity against gram positive and negative bacteria. Those are utilizable in treatment or prevention of infections caused by sensitive strains, for example, on administering a daily dose of 10 mg to 2 g to humans by intravenous injection. Oral or external agents may be prepared by mixing with conventional additives in a conventional manner.

Compounds (I) are also useful as intermediates for preparing other antibacterial agents.

As is disclosed above, the compounds (I) are valuable antibacterials against various gram positive and negative bacteria, and useful as drugs for human and veterinary uses. They can be used for treating or preventing infections caused by gram positive bacteria (e.g. *Staphylococcus aureus, Staphylococcus pyogenes, Bacillus subtilis, Bacillus cereus, Diplococcus pneumoniae*) and gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella typhi, Serratia marsescens*) and some are moderately active even against Pseudomonas species. The compounds can be used also as disinfectants for preventing bacterial growth of perishables, feedstuffs, or hygenical materials.

The compounds (I) can be used in a wide variety of oral or parenteral dosage forms solely or in admixture with other coacting substances. The pharmaceutical compositions may be a mixture of 0.01 to 99% of Compounds (I) with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injections, ointments, dispersions, inhalant, suspensions, solutions, emulsions, syrups, or elixirs. They may be flavored, colored, and tablets, granules, and capsules may be coated. All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrups, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate, emulsifying agents (e.g. lecithin, sorbitan monooleate, acacia); suspending agents (e.g. sorbitol, methylcellulose, glucose, or sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, analgesics, dispersing agents, wetting agents, antioxidants, and the like can be used if the agents do not exert adverse effect on the compounds, according to the methods conventional in the art.

Compounds (I), particularly their carboxylic acid salts, are soluble in water, and conveniently used as solution for intravenous, intramuscular, or subcutaneous injection according to a conventional method. The compounds can be dissolved in aqueous or oily solvents for injection to give a solution in an ampoule, but generally, more prolonged storage are possible by making a vial preparation containing crystals, powder, microcrystals, or lyophilizate of Compound (I), and dissolving or suspending the drug before use with the said solvents for injection. The preparation may contain preferably said preservative. The vial preparation or injection can be given to a patient at a daily dose of e.g. 0.1 to 100 mg/kg body weight depending on the infected bacteria, condition of the patient, and interval of the administration.

Compounds (I), especially those having $COR^3$ being a pharmaceutically acceptable ester grouping (e.g. indanyl, acetoxymethyl, pivaloyloxymethyl, ethoxycarbonyloxymethyl, phenacyl, phthalidyl, phenyl, tolyl, xylyl, methoxyphenyl esters), can be absorbed through the digestive organ to some extent, and can be administered to human or veterinary subjects as powder, tablets, granules, capsules, dry syrup, emulsions, solution, suspension and like oral preparations. These may be pure compounds or a composition comprising Compounds (I) and said pharmaceutical carriers. The preparation can be made according to the methods conventional in the art, and can be administered to a patient at a daily dose of e.g 1 to 50 mg/kg body weight depending on the condition of patient and disease.

Further, Compounds (I) can be used as suppositories, ointments for topical or ocular use, powders for topical use, and like preparations preparable according to methods well known to those skilled in the art. The external preparation can contain 0.01 to 99% of the Compound (I) together with a necessary amount of pharmaceutical carrier given above. A necessary amount e.g. 1 μg to 1 mg of the preparation can be applied to the infected part.

This invention also provides a method for treating or preventing human or veterinary bacterial infections by administering to the human or animal subject an effective amount of Compound (I) at a daily dose of e.g. 0.5 to 10 mg/kg body weight for injection or e.g 0.5 to 50 mg/kg body weight for oral administration, or 1 μg to 1 mg for topical application at an interval of e.g. 3 to 12 hours.

The method is applicable for treating or preventing some diseases caused by bacteria sensitive to Compounds (I) e.g. pneumoniae, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infections, and pyelonephritis.

Preferably the Compounds (I) are given to a patient in forms of pharmaceutical preparations e.g. powder, dry syrup, tablets, troches, granules, capsules, pills, suppositories, injections, ointments, dispersions, inhalant, suspensions, solutions, emulsions, syrups, and elixirs. They may be in a unit dosage form e.g. tablets, troches, capsules, injections, vials, granules or powder in a separate container or package.

The following examples are provided to further illustrate this invention.

EXAMPLE 1

A solution of 268 mg of D-N-(4-ethyl-2,3-dioxopiperazin-1-yl)carbonyl-α-p-hydroxyphenylglycine in a mixture of 20 ml of oxalyl chloride and 0.006 ml of dimethylformamide is added to 4 ml of dioxane, and the mixture stirred at room temperature for 1.5 hours and evaporated under reduced pressure. The residue is dissolved in dry dioxane, mixed with 0.20 ml of propylene oxide and 191 mg of diphenylmethyl 7α-methoxy-7β-amino-3-(1-methyl-1H-tetrazol-5-yl) thiomethyl-3-cephem-4-carboxylate with stirring at 0° C. and continued to stir at 0° C. for 20 minutes and then at room temperature for 2 hours. The reaction mixture is diluted with methylene chloride, washed with aqueous sodium hydrogencarbonate solution, dried and evaporated under reduced pressure to yield 240 mg of diphenylmethyl 7α-methoxy-7β-[N-(4-ethyl-2,3-dioxopiperazin-1-yl)carbonyl-α-p-hydroxyphenylglycyl]amino-3-(1-methyl-1H-tetrazol-5-yl)thiomethyl-3-cephem-4-carboxylate.

IR: $\nu_{max}^{KBr}$: 3300, 1780, 1710, 1680 cm$^{-1}$

NMR: $\delta_{ppm}^{CDCl3CD3OD(1:1)}$: 1.18t(7 Hz)3H, 3.48s3H, 3.40–4.40 ml OH, 3.80s3H, 5.03s1H, 5.15s1H, 5.40s1H, 6.80d(8 Hz)2H, 6.89s1H.

The identical product may also be prepared on reduction of 165 mg of diphenylmethyl 7α-methoxy-7β-[N-(4-ethyl-2,3-dioxopiperazin-1-yl)carbonyl-α-p-hydroxyphenylglycyl]amino-3-(1-methyl-1H-tetrazol-5-yl)thiomethyl-3-cephem-4-carboxylate-1-oxide in 3 ml of N,N-dimethylformamide with phosphorus trichloride at room temperature.

EXAMPLE 2

To a suspension of 340 mg of 7α-methoxy-7β-(p-hydroxyphenyl) glycylamino-3-(1-methyl-1H-tetrazol-5-yl)thiomethyl-3-cephem-4-carboxylic acid trifluoroacetate in 80 ml. of acetonitrile are added 1.0 ml of propylene oxide and then 0.6 ml of O,N-bis(trimethylsilyl) acetamide, and the mixture stirred at 0° C. for 20 minutes and mixed with 150 mg of 4-ethyl-2,3-dioxo-1-piperazinylcarbonyl chloride. The mixture is stirred at the same temperature for 1 hour and then at room temperature for 1 hour, and mixed with ethyl acetate and aqueous sodium hydrogencarbonate solution. The aqueous layer is separated, washed with ethyl acetate and adjusted to pH 2. The precipitate is filtered off to yield 7α-methoxy-7β-[N-(4-ethyl-2,3-dioxopiperazin-1-yl)carbonyl-α-p-hydroxyphenylglycyl]amino-3-(1-methyl-1H-tetrazol-5-yl)thiomethyl-3-cephem-4-carboxylic acid in the filtrate.

IR: $\nu_{max}^{KBr}$: 3300, 1700, 1660–1710 cm$^{-1}$

NMR: $\delta_{ppm}^{CDCl3}$: 1.17t(7 Hz)3H, 3.50s3H, 3.40–4.50 ml OH, 4.00s3H, 5.03s1H, 5.30s1H, 5.50s1H, 6.88d(7 Hz)2H, 7.40d(7 Hz)2H, 9.70s1H.

The identical product may also be prepared from 7α-methoxy-7β-[N-(4-ethyl-2,3-dioxopiperazin-1-yl)-α-p-carbamoyloxyphenylglycyl]amino-3-(1-methyl-1H-tetrazol-5-yl)thiomethyl-3-cephem-4-carboxylic acid on treatment with dilute aqueous sodium hydroxide solution.

EXAMPLE 3

To a solution of diphenylmethyl 7α-methoxy-7β-[N-(4-ethyl-2,3-dioxopiperazin-5-yl)carbonyl-α-p-hydroxyphenylglycyl]amino-3-(1-methyl-1H-tetrazol-5-yl)thiomethyl-3-cephem-4-carboxylate in 2 ml of methylene chloride are added 0.3 ml of anisole and 0.5 ml of trifluoroacetic acid at 0° C., and the mixture stirred for 2 hours, mixed with benzene and evaporated under reduced pressure. The residue is washed with ethyl acetate and then dissolved in acetone. The insoluble materials are filtered off and the filtrate is evaporated under reduced pressure to yield 95 mg of 7α-methoxy-7β-[N-(4-ethyl-2,3-dioxopiperazin-5-yl)carbonyl-α-(p-hydroxyphenyl)]glycylamino-3-(1-methyl-1H-tetrazol-5-yl)thiomethyl-3-cephem-4-carboxylic acid as powder.

This product is identical with one prepared in Example 2.

The identical product may also be prepared as follows: To a solution of 150 mg of 7α-methoxy-7β-[N-(4-ethyl-2,3-dioxopiperazin-1-yl)carbonyl-α-p-hydroxyphenylglycyl]aminocephalosporanic acid in 5 ml of dioxane is added 60 mg of 1-methyl-1H-tetrazol-5-thiol, and the mixture reacted in 5 ml of sodium hydrogencarbonate-sodium phosphate buffer (pH 6.2) at 50° C. for 6 hours.

EXAMPLE 4

To a suspension of 90 mg of N-(4-ethyl-2,3-dioxopiperazin-1-yl)carbonyl-α-p-acetoxyphenylglycine in 4 ml of benzene are added 50 μl of oxalyl chloride and 3 μl of N,N-dimethylformamide, and the mixture reacted at room temperature for 1 hour to yield the acid chloride compound, and the latter dissolved in methylene chloride, mixed with 53 mg of diphenylmethyl 7α-methoxy-7β-amino-3-(1-methyl-1H-tetrazol-5-yl)thiomethyl-3-cephem-4-carboxylate and 0.2 ml of propylene oxide under ice-cooling, stirred at room temperature for 1 hour, poured into aqueous sodium hydrogencarbonate solution and then extracted with methylene chloride. The extract is washed with water, dried and evporated. The residue is chromatographed on 10 g of silica gel containing 10% water and eluted with benzene-ethyl acetate (1:1) to yield 58 mg of diphenylmethyl 7β-[α-p-acetoxyphenyl-N-(4-ethyl-2,3-dioxopiperazin-1-yl)carbonylglycyl]amino-7α-methoxy-3-(1-methyl-1H-tetrazol-5-yl)thiomethyl-3-cephem-4-carboxylate.

IR: $\nu_{max}^{CHCl_3}$: 3400, 1788, 1742, 1730 cm$^{-1}$

To a solution of 56 mg of diphenylmethyl ester prepared above in 2 ml of methylene chloride are added 0.15 ml of anisole and 0.1 ml of trifluoroacetic acid, and the mixture allowed to stand at 0° C. for 1 hour and evaporated under reduced pressure. The residue is agitated in ether to yield 30 mg of 7α-methoxy-7β-[α-p-acetoxyphenyl-N-(4-ethyl-2,3-dioxopiperazin-1-yl)carbonylglycyl]amino-3-(1-methyl-1H-tetrazol-5-yl)thiomethyl-3-cephem-4-carboxylic acid.

IR: $\nu_{max}^{KBr}$: 3320, 1775, 1745, 1732 cm$^{-1}$

The identical product may also be prepared from the compound in Example 2 on reaction with acetic anhydride in methylene chloride in the presence of triethylamine at room temperature overnight.

EXAMPLE 5

To a solution of 100 mg of diphenylmethyl 7α-methoxy-7β-[N-(4-ethyl-2,3-dioxopiperazin-1-yl)carbonyl-α-p-hydroxyphenyl]glycylamino-3-(1-methyl-1H-tetrazol-5-yl)thiomethyl-3-cephem-4-carboxylate in 4 ml of methylene chloride is added 0.5 ml of tri- chloroacetylisocyanate under ice-cooling, and the mixture stirred for 2 hours, mixed with methylene chloride, and poured into ice water. The reaction mixture is washed with water, dried over magnesium sulfate and evaporated. The residue is dissolved in 3 ml of chloroform, adsorbed on silica gel containing 10% water, allowed to stand for 30 minutes and eluted with chloroform-methanol (20:1) to yield 82 mg of diphenylmethyl 7α-methoxy-7β-[N-(4-ethyl-2,3-dioxopiperazin-1-yl)carbonyl-α-p-carbamoyloxyphenylglycyl]amino-3-(1-methyl-1H-tetrazol-5-yl)thiomethyl-3-cephem-4-carboxylate (78% yield).

NMR: $\delta_{ppm}^{CDCl_3}$ 1.10t(7 Hz)3H, 3.20–4.40 ml OH, 3.45s3H, 3.74s3H, 5.00s1H, 5.60br3H, 6.87s1H, 7.07d(8 Hz)2H, 9.83brs1H.

To a solution of 60 mg of the diphenylmethyl ester compound prepared above in 0.5 ml of methylene chloride are added 0.1 ml of anisole and 0.1 ml of trifluoroacetic acid, and the mixture stirred at the same temperaure for 2 hours and evaporated under reduced pressure. The obtained residue is washed with ether and then ethyl acetate to yield 40 mg of 7α-methoxy-7β-[N-(4-ethyl-2,3-dioxopiperazin-1-yl)carbonyl-α-p-carbamoyloxyphenylglycyl]amino-3-cephem-4-carboxylic acid as powder (82% yield).

EXAMPLE 6

The following compounds may also be prepared in the same manners as described in Examples 1 to 5.

| No. | R$^1$ | R$^2$ | R$^3$ |
|---|---|---|---|
| 1 | H | CH$_3$ | OH |
| 2 | COC$_2$H$_5$ | C$_2$H$_5$ | OH |
| 3 | COC$_6$H$_5$ | C$_2$H$_5$ | OCH(C$_6$H$_5$)$_2$ |
| 4 | CONH$_2$ | n-C$_3$H$_7$ | OH |
| 5 | CONH$_2$ | i-C$_4$H$_9$ | OCH$_2$C$_6$H$_5$ |
| 6 | CONH$_2$ | CH$_2$CH(CH$_3$)$_2$ | OCH$_2$C$_6$H$_4$NO$_2$-p |
| 7 | CSNH$_2$ | C$_2$H$_5$ | OCH(C$_6$H$_5$)$_2$ |
| 8 | CSNH$_2$ | C$_2$H$_5$ | OH |
| 9 | CSNHCH$_3$ | C$_2$H$_5$ | OH |
| 10 | CON(CH$_3$)$_2$ | C$_2$H$_5$ | OH |
| 11 | CONHCOCCl$_3$ | C$_2$H$_5$ | OCH$_2$C$_6$H$_4$OCH$_3$-p |
| 12 | CONHCOCH$_3$ | CH$_3$ | OCH(C$_6$H$_5$)$_2$ |

EXAMPLE 7

Free acids found in Examples 2 to 5 are dissolved in dilute aqueous sodium hydrogencarbonate solution to yield the corresponding aqueous sodium salts solutions. All of them exhibit potent antibacterial activity against β-lactamase-producing bacteria when tested in vitro.

For example, a compound represented by the following formula, wherein Y is methoxy, exhibits more potent antibacterial activity against gram negative bacteria resistant to cephalosporins than that wherein Y is hydrogen.

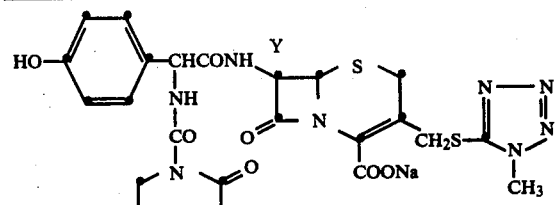

| | Antibacterial Activity | | | | | |
|---|---|---|---|---|---|---|
| | (MIC:γ/cc) | | | | | |
| Y | H | | OCH$_3$ | | cefoxitin | |
| innoculum size | $10^6$ | $10^8$ | $10^6$ | $10^8$ | $10^6$ | $10^8$ |
| bacteria | | | | | | |
| *Escherichia coli* No. 73 | 25 | >100 | 1.6 | 3.1 | 12.5 | 12.5 |
| *Klebsilla pneumoniae* No. 363 | 100 | >100 | 0.8 | 1.6 | 1.6 | 6.3 |

EXAMPLE 8

Sodium 7α-methoxy-7β-[N-(4-ethyl-2,3-dioxopiperazin-1-yl)carbonyl-α-p-hydroxyphenylglycyl]amino-3-(1-methyl-1H-tetrazol-5-yl)thiomethyl-3-cephem-4-carboxylate (100 mg) in a 5 ml vial is dissolved in sterilized water for injection (1 ml) before use, and injected intravenously to an adult patient suffering from infections caused by *Klebsiella pneumoniae.*

EXAMPLE 9

Butoxycarbonyloxyethyl 7α-methoxy-7β-[N-(4-ethyl-2,3-dioxopiperazin-1-yl)carbonyl-α-p-hydroxyphenylglycyl]amino-3-(1-methyl-1H-tetrazol-5-yl)thiomethyl-3-cephem-4-carboxylate (100 mg) is mixed with corn starch (150 mg) and talc (10 mg), powdered and encapsulated in a hard gelatin capsule (250 mg volume). Each one capsule is administered orally at 3 hour intervals to an adult patient suffering from infections caused by *Escherichia coli.*

We claim:
1. A member selected from the group consisting of
(a) a compound of the formula:

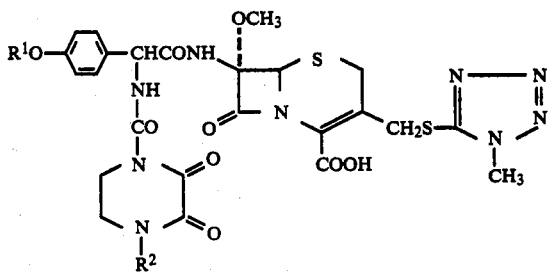

wherein
R$^1$ represents hydrogen, carbamoyl, acetyl, propionyl, butyryl, benzoyl, thiocarbamoyl, methylthiocarbamoyl, dimethylcarbamoyl, trichloroacetylcarbamoyl, acetylcarbamoyl, methoxycarbonyl, ethoxycarbonyl, propoxycarbonyl, or isopropoxycarbonyl;
R$^2$ represents methyl, ethyl, propyl, isopropyl, butyl, isobutyl, secondary-butyl, or tertiary-butyl;
(b) a lithium, sodium, potassium, magnesium, calcium or aluminum salt thereof at the 3-carboxy, and (c) an acetoxymethyl, pivaloyloxymethyl, methoxycarbonyloxymethyl, ethoxycarbonyloxyethyl, butoxycarbonyloxymethyl, phenacyl, phenyl, indanyl or phthalidyl ester thereof at the 3-carboxy.
2. A compound claimed in claim 1 wherein R$^1$ is hydrogen and R$^2$ is methyl.
3. A compound claimed in claim 1 wherein R$^1$ is hydrogen and R$^2$ is ethyl.
4. A compound claimed in claim 1 wherein R$^1$ is hydrogen and R$^2$ is propyl.
5. A compound claimed in claim 1 wherein R$^1$ is hydrogen and R$^2$ is isopropyl.
6. A compound claimed in claim 1 wherein R$^1$ is hydrogen and R$^2$ is butyl.
7. A compound claimed in claim 1 wherein R$^1$ is hydrogen and R$^2$ is secondary-butyl.
8. A compound claimed in claim 1 wherein R$^1$ is hydrogen and R$^2$ is isobutyl.
9. A compound claimed in claim 1 wherein R$^1$ is hydrogen and R$^2$ is tertiary-butyl.
10. A compound claimed in claim 1 wherein R$^1$ is carbamoyl and R$^2$ is methyl.
11. A compound claimed in claim 1 wherein R$^1$ is carbamoyl and R$^2$ is ethyl.
12. A compound claimed in claim 1 wherein R$^1$ is carbamoyl and R$^2$ is propyl.
13. A compound claimed in claim 1 wherein R$^1$ is carbamoyl and R$^2$ is butyl.
14. A compound claimed in claim 1 wherein R$^1$ is carbamoyl and R$^2$ is isobutyl.
15. A compound claimed in claim 1 wherein R$^1$ is acetyl and R$^2$ is methyl.
16. A compound claimed in claim 1 wherein R$^1$ is acetyl and R$^2$ is ethyl.
17. A compound claimed in claim 1 wherein R$^1$ is acetyl and R$^2$ is propyl.
18. A compound claimed in claim 1 wherein R$^1$ is acetyl and R$^2$ is isobutyl.
19. A compound claimed in claim 1 wherein R$^1$ is propionyl and R$^2$ is methyl.
20. A compound claimed in claim 1 wherein R$^1$ is propionyl and R$^2$ is ethyl.
21. A compound claimed in claim 1 wherein R$^1$ is propionyl and R$^2$ is propyl.
22. A compound claimed in claim 1 wherein R$^1$ is butyryl and R$^2$ is methyl.
23. A compound claimed in claim 1 wherein R$^1$ is butyryl and R$^2$ is ethyl.
24. A compound claimed in claim 1 wherein R$^1$ is benzoyl and R$^2$ is methyl.
25. A compound claimed in claim 1 wherein R$^1$ is benzoyl and R$^2$ is ethyl.
26. A compound claimed in claim 1 wherein R$^1$ is thiocarbamoyl and R$^2$ is ethyl.
27. A compound claimed in claim 1 wherein R$^1$ is methylthiocarbamoyl and R$^2$ is ethyl.
28. A compound claimed in claim 1 wherein R$^1$ is dimethylcarbamoyl and R$^2$ is ethyl.
29. A compound claimed in claim 1 wherein R$^1$ is trichloroacetylcarbamoyl and R$^2$ is ethyl.
30. An antibacterial composition which comprises an antibacterially effective amount of a member of the group as defined in claim 1 and a pharmaceutically acceptable carrier.
31. A method for the treatment of a bacterial infection which comprises administering orally or parenterally to a human or animal subject suffering from said infection an antibacterially effective amount of a composition as defined in claim 30.

* * * * *